(12) United States Patent
Weckbecker et al.

(10) Patent No.: US 7,179,938 B2
(45) Date of Patent: Feb. 20, 2007

(54) PROCESS FOR THE PREPARATION OF METHIONINE

(75) Inventors: Christoph Weckbecker, Gründau-Lieblos (DE); Horst Krull, Hanau (DE); Jürgen Bilz, Freigericht (DE); Klaus Huthmacher, Gelnhausen (DE); Hans Joachim Hasselbach, Gelnhausen (DE)

(73) Assignee: Degussa AG, Düsseldorf (DE)

( * ) Notice: Subject to any disclaimer, the term of this patent is extended or adjusted under 35 U.S.C. 154(b) by 373 days.

(21) Appl. No.: 10/497,949

(22) PCT Filed: Aug. 6, 2002

(86) PCT No.: PCT/EP02/08742

§ 371 (c)(1),
(2), (4) Date: Jun. 7, 2004

(87) PCT Pub. No.: WO03/050071

PCT Pub. Date: Jun. 19, 2003

(65) Prior Publication Data

US 2005/0131111 A1   Jun. 16, 2005

(30) Foreign Application Priority Data

Dec. 8, 2001   (DE) ................. 101 60 358

(51) Int. Cl.
*C07C 323/00* (2006.01)
*C07C 57/00* (2006.01)

(52) U.S. Cl. ...................................... 562/559; 554/227

(58) Field of Classification Search .................... None
See application file for complete search history.

(56) References Cited

U.S. PATENT DOCUMENTS

| 3,917,683 A | 11/1975 | Ouchi et al. |
| 5,681,692 A | 10/1997 | Orem et al. |
| 5,990,349 A | 11/1999 | Geiger et al. |

FOREIGN PATENT DOCUMENTS

| GB | 1 080 220 A | 8/1967 |
| JP | 01-288267 | 11/1989 |
| JP | 03-266979 | 11/1991 |
| JP | 04-244056 | 9/1992 |
| KR | 9104482 B | * 7/1991 |

* cited by examiner

*Primary Examiner*—Paul A. Zucker
(74) *Attorney, Agent, or Firm*—Smith, Gambrell & Russell, LLP

(57) ABSTRACT

The invention relates to a process for the preparation of methionine of high bulk density, in which a mixture which comprises a compound which has a foaming action and a compound which influences the crystallization is added to the hydrolysis solution, and to the mixture itself.

23 Claims, No Drawings

PROCESS FOR THE PREPARATION OF METHIONINE

INTRODUCTION AND BACKGROUND

The invention relates to a process for the preparation of methionine of high bulk density, in which a mixture which comprises a compound which has a foaming action and a compound which influences crystallization is added to the hydrolysis solution, and to the mixture itself.

It is known that the preparation of amino acids is often associated with difficulties. Handling of solutions or suspensions containing amino acids already leads to severe foaming in laboratory processes, but above all of course in industrial production. This undesirable effect can lead not only to the production proceeding in a very problematic manner and with poor space/time yields, but in individual cases also to failure of an economical production of the amino acid.

JP 09000241 thus describes that the addition of various additives from the family of nitrogen-containing polyoxyalkylenes in the fermentative production of amino acids leads to a reduction in foaming. JP 09000241 relates to the preparation of defoamer mixtures which are composed of fats or oils and the reaction products of fatty acids or derivatives thereof and polyalcohols with alkylene oxides. These mixtures are suitable for use in fermentations. It is known that the yield of lysine and tryptophan production can be increased if silicone are used as foam-destroying additives, instead of sunflower oil. The influence of various silicone oils is investigated by comparison in Khim.-Farm. Zh (1972), 6(5), 27–30.

In the carbonate process known from EP 0 780 370, methionine is obtained on acidification of a solution of potassium methioninate with carbon dioxide in accordance with the equation

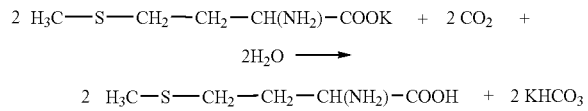

Methionine is in general precipitated out of these solutions in the form of very flat leaflets, separating off of which proceeds only very slowly and therefore uneconomically.

There are therefore attempts to influence the crystallization properties of the methionine by addition of particular auxiliary substances.

It is demonstrated in JP-11-158140 that the use of various auxiliary substances, such as hydroxymethylpropylcellulose, sorbitan monolaurate or polyvinyl alcohols, influences the crystal habit, and the bulk density of the methionine obtained in this way increases.

These compounds are added in an amount of at least 500 ppm during the crystallization, which is carried out continuously and proceeds in two stages under specific stirring conditions. A round-particled methionine is obtained.

No additive or mixture of additives with the aid of which at the same time the foam which forms in the various stages of methionine preparation can be suppressed and the crystal habit of the methionine which has precipitated out, in particular in the carbonate process, can be improved is known from the prior art.

SUMMARY OF THE INVENTION

The present invention is based on the object of minimizing the formation of foam in the methionine process and at the same time positively influencing the crystal habit of the methionine which has precipitated out after the recrystallization.

The invention provides an aqueous mixture which comprises compounds of the general formula (additive (1))

$$C_nH_{2n+x}C=O-O-[CH_2-CH_2-O]_m-H \qquad (1),$$

in which the symbols denote:

n: an integer from 9 to 19, preferably 15 to 17, m: a distribution in the range from 1 to 10, wherein the maximum is preferably 5 to 8, in particular 6 to 7, x: 1, −1, −3, −5, wherein 2n+x is not less than 1, and additives (2) from the group consisting of modified celluloses, in particular methylcellulose, methylhydroxycellulose, methylhydroxypropylcellulose, hydroxypropylcellulose, hydroxyethylcellulose, sodium carboxymethylcellulose, sodium carboxymethylhydroxyethylcellulose and sodium carboxymethylhydroxypropylcellulose in a weight ratio of 1:10 to 10:1, preferably 1:3 to 3:1.

The fatty acid contents in compounds according to formula (1) are preferably of natural origin, and are saturated or unsaturated, depending on the meaning of x.

The mixture is advantageously employed in the form of an aqueous solution or emulsion with a total additive content of 1 to 5 wt. %, in particular 2 to 4 wt. %, based on the total amount.

In order to produce a stable emulsion, it is merely necessary to treat the mixture with a conventional blade stirrer. Since hydroxycelluloses dissolved in water can lead to highly viscous solutions, it is advantageous to use low molecular weight hydroxycelluloses with a viscosity of <300 mPas (as a 2% solution in water). The viscosity can furthermore also be adjusted via the degree of dilution.

Preferably, an aqueous solution or emulsion of the additives (1) and (2) with a viscosity of between 5 and 5000 mPas, based on a 2% solution of the additives in water, in particular 10 to 500 mPas, is prepared by dissolving or emulsifying the compounds according formula (1) and (2) in the desired amount.

It has been found that the mixture described is suitable for reducing the foaming in process solutions obtained during the preparation of methionine and at the same time effecting the formation of larger crystals during the recrystallization.

One important aspect of the invention is that the defoaming action and the crystallization can be controlled by changing the ratios of amounts of (1) to (2) in the mixture.

Foaming depends greatly on the composition of the process solutions and the other process conditions, such as, for example, pressure and temperature.

The mixtures according to the invention already display their defoaming and a crystal growth-promoting action when small amounts are added. Amounts of 10 to 500 ppm, based on the methionine, are already active.

At the same time, it is to be found that the compounds (1) and (2) employed according to the invention have no adverse influence on the action of the other particular compounds.

On the contrary, it is the case that the interaction of (1) and (2) can lead to an improvement in the crystal structure (see, for example, image no. 1703045).

The invention also provides a process for the preparation of methionine, in particular with a purity of 80 to 100 wt. %, by reaction of the components 3-methylmercaptopropionaldehyde, hydrogen cyanide, ammonia and carbon dioxide or of those components from which the above-mentioned components can be prepared, optionally in the presence of water, to give 5-(2-methylmercaptoethyl)-hydantoin and conversion thereof into methionine, which is characterized in that, before carbon dioxide is passed in, an aqueous mixture which comprises compounds of the general formula

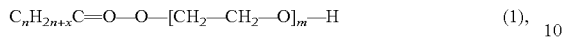

$$C_nH_{2n+x}C=O-O-[CH_2-CH_2-O]_m-H \qquad (1),$$

in which the symbols denote:
n: an integer from 9 to 19, preferably 15, 17 or 19,
m: a distribution in the range from 1 to 10, wherein the maximum is preferably 5 to 8, in particular 6 to 7,
x: 1, −1, −3, −5, wherein 2n+x is not less than 1, and additives (2) from the group consisting of modified celluloses, in particular methylcellulose, methylhydroxycellulose, methylhydroxypropylcellulose, hydroxypropylcellulose, hydroxyethylcellulose, sodium carboxymethylcellulose, sodium carboxymethylhydroxyethylcellulose and sodium carboxymethylhydroxypropylcellulose, is added to the hydrolysis solution obtained from 5-(2-methylmercaptoethyl)-hydantoin in a weight ratio of 1:10 to 10:1, preferably 1:3 to 3:1, in a total amount of 5 to 5000 ppm, preferably 5 to 500 ppm, based on the methionine (wt. %) contained in the solution, and the methionine which has precipitated out is dissolved and, in particular using the mother liquor, which preferably comprises the additives (1) and (2) mentioned, is crystallized in the presence of crystalline methionine, optionally with the addition of further amounts of the aqueous mixture.

According to the invention, the high stirring energy known from the prior art does not have to be introduced during the precipitation or the crystallization. The same applies to the $CO_2$ pressures known from the prior art. Only a uniform distribution of the carbon dioxide, which has been introduced, during the precipitation of the methionine into the hydrolysis solution remains essential.

The process claimed can be carried out continuously or discontinuously.

During the precipitation of the methionine, with the addition of carbon dioxide, from the solution obtained as the hydrolysis product, the additive (1) has a defoaming action, while at the same time the presence of (2) has no adverse influence on the defoaming.

The recrystallization is preferably carried out by a procedure in which, preferably, methionine suspended in the mother liquor is pumped in circulation at a temperature of 30 to 60° C., and a methionine solution which has a concentration of 70 to 150 g/l, in particular 90 to 130 g/l, and has been heated up to 60 to 110° C., in particular 80 to 100° C., is admixed to this suspension. The methionine solution mentioned last optionally comprises a content of 5 to 20 vol. % of mother liquor from the preparation process.

Methionine precipitates out in the desired purity by the cooling. Methionine with a purity of 80 to 100 wt. %, in particular 90 to 100 wt. %, which is not to be achieved in one-stage processes, is obtained with this step of recrystallization.

The ration of amounts between the suspension pumped in circulation and the solution admixed is in general 1–10:1, in particular 2–6:1, preferably 3–5:1.

The mixture claimed simplifies the process in the respect that during the precipitation of the methionine from the hydrolysis solution and the recrystallization of the methionine which has precipitated out, this same mixture which comprises compound (1) and (2) can be employed.

However, the constituents (1) and (2) can also be added individually. (2) in particular displays its properties in particular during the crystallization.

DETAILED DESCRIPTION OF INVENTION

The invention is illustrated by the following examples.

EXAMPLE 1

Precipitation with Carbon Dioxide

A 4% emulsion of hydroxyethylcellulose, which has a viscosity of 200 mPas (V=200) as a 2% solution, in water, and stearic acid ester 1 (n=17; m=7) in a weight ratio of 1:1 are introduced, while stirring, into 1 L of a solution of potassium methioninate and potassium bicarbonate with a methionine concentration of 70 g/l and a potassium concentration of 150 g/l, such that an emulsion which comprises 50 ppm of additives is formed. Carbon dioxide is fed in at pH=11 under a pressure of 2 bar in a 2 L autoclave at a stirrer speed of 500 rpm. The addition of carbon dioxide is continued at 30° C. until the pH is reduced to 8.0. Foam forms on the reaction mixture at a height of 1 centimeter, while at the same time methionine is precipitated.

EXAMPLE 2

Recrystallization 60 g methionine are suspended at 40° C. in 300 ml water and 40 g filtrate of the mother liquor from the precipitation with carbon dioxide and the suspension is pumped in circulation. A 4% emulsion of hydroxyethylcellulose, which has a viscosity of 200 mPas (V=200) as a 2% solution, in water, and stearic acid ester 1 (n=18; m=7) in a weight ratio of 1:1 are introduced, while stirring, into this suspension such that an emulsion which comprises 50 ppm of additives is formed. A heat exchanger is connected in series in order to keep the temperature constant. A hot solution at 90° C. of 180 g methionine in 1170 g water and 150 g filtrate of the mother liquor from the precipitation with carbon dioxide is added to this solution with a rate of 1 liter of solution per hour. The recrystallization of the methionine, which has precipitated out, in the presence of 50 ppm of the additives (total amount), based on the methionine, leads to crystals with a bulk density of 586 g/l.

The SEM photograph with the image number 173029 shows the coarsely crystalline structure of the end product obtained in this way.

Methionine precipitates out due to the cooling. 0.6 liter of the hot solution is added, 500 ml of the circulating suspension are removed and a further 500 ml of hot solution are added. The suspension is filtered off, the solid is rinsed with 300 ml acetone and dried to constant weight at 60° C. in a vacuum drying cabinet and the bulk density is determined.

A 4% emulsion of hydroxyethylcellulose, which has a viscosity of 200 mPas (V=200) as a 2% solution, in water, and stearic acid ester 1 (n=18; m=7) in a weight ratio of 1:1 are introduced, while stirring, into this solution which has been added dropwise, such that an emulsion which comprises 50 ppm of additives is formed.

EXAMPLE 3

Further Experiments

Further experiments which were carried out in accordance with Examples 1 and 2 are summarized in Table 1. Deviating experimental conditions are to be found underneath the table.

TABLE 1

| Experiment no.: | Compound (1) | Additive (2) (viscosity) | Mixt (ppm) | Weight ratio (1):(2) | Foam height [cm] | Bulk density [g/l] |
|---|---|---|---|---|---|---|
| 1 | — | — | — | — | 15 | 420 |
| 2 | n = 18; m = 7 | — | 160 | — | 1 | 470 |
| 3 | — | hydroxymethyl-cellulose (200) | 50 | — | 11 | 620 |
| 4 | n = 18; m = 7 | hydroxymethyl-cellulose (200) | 50 | 1:1 | 1 | 586 |
| 5 | n = 18; m = 7 | hydroxymethyl-cellulose (300) | 400 | 1:1 | 2 | 586 |
| 6 | n = 18; m = 7 | hydroxymethyl-cellulose (300) | 400 | 2:1 | 2 | 571 |
| 7 | n = 18; m = 7 | hydroxymethyl-cellulose (300) | 400 | 1:1 | 3 | 581 |
| 8 | n = 18; m= 7 | hydroxymethyl-cellulose (300) | 50 | 1:1 | 3 | 572 |
| 9 | n = 18; m = 7 | hydroxymethyl-cellulose (300) | 400 | 1:2 | 2 | 576 |

Experiment 1: 71 g/l methionine and 175 g/l potassium in the solution
Experiment 8: Viscosity of additive 2 is 75–150 mPas at 25° C.
Mixtures (ppm): Concentration of the mixture in the hydrolysis mixture
SEM photographs are attached for documentation of the advantageous results which are achieved with this invention.

It is found that without the addition of additives (1) and (2), a fine-particled methionine is obtained after the recrystallization (image no.: 170867).

The use of compound (1), which in general has a defoaming action, also leads to no substantial coarsening of the crystal structure (image no.: 170875).

The optimum results according to the invention are found only when additives (2) are employed together with (1) (image no.: 173029).

A comparison with image no. 173045 shows that the sole use of (2) already leads to results which exceed the prior art, but the addition of (1) has the effect of a further improvement.

Further variations and modifications of the foregoing will be apparent to those skilled in the art and are intended to be encompassed by the claims appended hereto.

German prior application No. 101 60 358.4 of Dec. 8, 2001, and PCT application No. PCT/EP02/08742 of Aug. 6, 2002, are relied on and incorporated herein by reference.

TABLE 2

| Image no.: | Name/additive | Total amount of additives | Bulk density | Magnification |
|---|---|---|---|---|
| 173029 | Additive (2) (HEC) (n = 18, m = 7) | 50 ppm | 586 g/l | 100:1 |
| 173045 | Additive (2) (HEC) | 50 ppm | 620 g/l | 100:1 |
| 170875 | Compound (1) (n = 18, m = 7) | 160 ppm | 470 g/l | 100:1 |
| 170867 | without (1) and (2) | — | 420 g/l | 100:1 |

What is claimed is:

1. An aqueous mixture which consists of water and compounds of the formula:

$$C_nH_{2n+x}C{=}O{-}O{-}(CH_2{-}CH_2{-}O)_m{-}H \quad (1),$$

in which the symbols denote:
n: an integer from 9 to 19,
m: from 1 to 10
x: 1, −1, −3, −5, wherein 2n+x is not less than 1,
and at least one additive which is a modified cellulose, in a weight ratio of 1:10 to 10:1.

2. The aqueous mixture according to claim 1, wherein n is 15, 17 or 19.

3. The aqueous mixture according to claim 1, wherein m is 5 to 8.

4. The aqueous mixture according to claim 3, wherein m is 6 or 7.

5. The aqueous mixture according to claim 1, wherein the modified cellulose is a member selected from the group consisting of methylcellulose, methylhydroxycellulose, methylhydroxypropylcellulose, hydroxypropylcellulose, hydroxyethylcellulose, sodium carboxymethylcellulose, sodium carboxymethylhydroxyethylcellulose and sodium carboxymethylhydroxypropylcellulose in a weight ratio of 1:10 to 10:1.

6. The aqueous mixture according to claim 1, which has a total additive content of 1 to 5 wt. %.

7. A process for the preparation of methionine comprising reacting a source of 3-methylmercaptopropionaldehyde, a source of hydrogen cyanide, a source of ammonia and a source of carbon dioxide, optionally in the presence of water, to form 5-(2-methylmercaptoethyl)-hydantoin and conversion thereof into methionine, wherein, before carbon dioxide is passed in, adding to a hydrolysis solution obtained from 5-(2-methylmercaptoethyl)-hydantoin in a weight ratio of 1:10 to 10:1, an aqueous mixture which comprises a compound of the formula (1):

$$C_nH_{2n+x}C{=}O{-}O{-}(CH_2{-}CH_2{-}O)_m{-}H \quad (1),$$

in which the symbols denote:
n: a number from 9 to 19, m: from 1 to 10, x: 1, −1, −3, −5, wherein 2n+x is not less than 1, and an additive which is a modified cellulose, in particular methylcellulose, methylhydroxycellulose, methylhydroxypropylcellulose, hydroxypropylcellulose, hydroxyethylcellulose, sodium carboxymethylcellulose, sodium carboxymethylhydroxyethylcellulose and sodium carboxymethylhydroxypropylcellulose, in a total amount of 5 to 5000 ppm based on the methionine contained in the solution, and dissolving methionine which has precipitated out and then recrystallizing to obtain the methionine.

8. The process according to claim 7, wherein m is 5 to 8.

9. The process according to claim 7, wherein m is 6 or 7.

10. The process according to claim 7, wherein the additive is at least one member selected from the group consisting of methylcellulose, methylhydroxycellulose, methylhydroxypropylcellulose, hydroxypropylcellulose, hydroxyethylcellulose, sodium carboxymethylcellulose, sodium carboxymethylhydroxyethylcellulose and sodium carboxymethylhydroxypropylcellulose.

11. The process according to claim 7, wherein the weight ratio is 1:3 to 3:1.

12. The process according to claim 7, wherein the total amount of 10 to 500 ppm.

13. The process according to claim 7, wherein recrystallizing is done using crystalline methionine suspended in mother liquor.

14. The process according to claim 7, wherein compound (1) in which n corresponds to 16, 18 or 20 is employed.

15. The process according to claim 7, wherein compound (1) in which m is 5 to 8 is employed.

16. The process according to claim 7, wherein compound (1) in which m is 6 or 7 is employed.

17. The process according to claim 7, wherein a compound (1) in which n=18 and m=7 is employed.

18. The process according to claim 7, wherein hydroxyethylcellulose is employed as additive.

19. The process according to claim 7, wherein hydroxyethylcellulose which has a viscosity of 200 mPas as a 1% solution is employed as additive.

20. The process according to claim 7, wherein the aqueous mixture comprising (1) and the additive is employed in the form of a pumpable emulsion in water.

21. The process according to claim 7, wherein the aqueous mixture comprising (1) and the additive is employed in the form of a 2–5% emulsion in water.

22. The process according to claim 7, wherein the aqueous mixture comprising (1) and the additive is employed in a concentration of 10 to 450 ppm of total additive concentration, based on methionine concentration.

23. The process according to claim 7, wherein during the recrystallizing, the aqueous mixture is added again in the desired amount.

* * * * *